(12) United States Patent
Haugen

(10) Patent No.: US 10,126,252 B2
(45) Date of Patent: Nov. 13, 2018

(54) ENHANCED ILLUMINATION CONTROL FOR THREE-DIMENSIONAL IMAGING

(71) Applicant: CyberOptics Corporation, Golden Valley, MN (US)

(72) Inventor: Paul R. Haugen, Bloomington, MN (US)

(73) Assignee: CyberOptics Corporation, Golden Valley, MN (US)

( * ) Notice: Subject to any disclaimer, the term of this patent is extended or adjusted under 35 U.S.C. 154(b) by 65 days.

(21) Appl. No.: 14/255,333

(22) Filed: Apr. 17, 2014

(65) Prior Publication Data

US 2014/0320633 A1    Oct. 30, 2014

Related U.S. Application Data

(60) Provisional application No. 61/816,990, filed on Apr. 29, 2013.

(51) Int. Cl.
*G01N 21/956* (2006.01)
*H04N 5/235* (2006.01)
*H04N 5/247* (2006.01)

(52) U.S. Cl.
CPC ......... *G01N 21/956* (2013.01); *H04N 5/2354* (2013.01); *H04N 5/247* (2013.01); *G01N 2021/95646* (2013.01)

(58) Field of Classification Search
CPC ..... G01N 21/95684; G01N 2021/8887; G01N 2021/95646; G01N 21/8806; G01N 21/956; G06T 2207/30152; G06T 2207/10152

(Continued)

(56) References Cited

U.S. PATENT DOCUMENTS 2,625,856 A   1/1953  Muller
3,777,061 A   12/1973 Takemura
(Continued)

FOREIGN PATENT DOCUMENTS

CN    1968597 A    5/2007
DE    4011407      10/1991
(Continued)

OTHER PUBLICATIONS

Search Report and Written Opinion from PCT application No. PCT/US2014/011762, dated May 12, 2014, 15 pages.

(Continued)

*Primary Examiner* — Jamie J Atala
*Assistant Examiner* — Ayman A Abaza
(74) *Attorney, Agent, or Firm* — Christopher R. Christenson; Kelly, Holt & Christenson PLLC

(57) ABSTRACT

A system for sensing a three-dimensional topology of a circuit board is provided. An illumination source generates patterned illumination from a first point of view. At least one camera acquires an image of the patterned illumination from a second point of view. A controller is coupled to the source, and to the at least one camera. The controller generates a height topology of the circuit board based on images acquired from first and second image detectors of the patterned illumination. The characteristics of the pattern illumination are modified based on knowledge of the circuit board to enhance the dynamic range of the sensor and to reject image defects caused by multipath reflections.

6 Claims, 10 Drawing Sheets

(58) Field of Classification Search
USPC .......................................................... 248/87
See application file for complete search history.

(56) References Cited

U.S. PATENT DOCUMENTS

| | | |
|---|---|---|
| 3,995,107 A | 11/1976 | Woywood |
| 4,541,010 A | 9/1985 | Alston |
| 4,593,967 A | 6/1986 | Haugen |
| 4,598,321 A | 7/1986 | Elabd et al. |
| 4,641,972 A | 2/1987 | Halioua et al. |
| 4,643,565 A | 2/1987 | Goto |
| 4,677,473 A | 6/1987 | Okamoto et al. |
| 4,782,394 A | 11/1988 | Hieda et al. |
| 4,835,616 A | 5/1989 | Morcom |
| 4,949,172 A | 8/1990 | Hunt et al. |
| 4,963,024 A | 10/1990 | Ulich |
| 4,984,893 A | 1/1991 | Lange |
| 5,039,868 A | 8/1991 | Kobayashi et al. |
| 5,069,548 A | 12/1991 | Boehnlein |
| 5,091,963 A | 2/1992 | Litt et al. |
| 5,103,105 A | 4/1992 | Ikegaya et al. |
| 5,135,308 A | 8/1992 | Kuchel |
| 5,278,634 A | 1/1994 | Skunes et al. |
| 5,298,734 A | 3/1994 | Kokubo |
| 5,307,152 A | 4/1994 | Boehnlein et al. |
| 5,406,372 A | 4/1995 | Vodanovic et al. |
| 5,424,552 A | 6/1995 | Tsuji et al. |
| 5,450,204 A | 9/1995 | Shigeyama et al. |
| 5,450,228 A | 9/1995 | Boardman et al. |
| 5,455,870 A | 10/1995 | Sepai et al. |
| 5,546,127 A | 8/1996 | Yamashita et al. |
| 5,555,090 A | 9/1996 | Schmutz |
| 5,636,025 A | 6/1997 | Bieman et al. |
| 5,646,733 A | 7/1997 | Bieman |
| 5,668,665 A | 9/1997 | Choate |
| 5,684,530 A | 11/1997 | White |
| 5,686,994 A | 11/1997 | Tokura |
| 5,691,784 A | 11/1997 | Hausler et al. |
| 5,708,532 A | 1/1998 | Wartmann |
| 5,761,337 A | 6/1998 | Nishimura et al. |
| 5,774,221 A | 6/1998 | Guerra |
| 5,815,275 A | 9/1998 | Svetkoff et al. |
| 5,862,973 A | 1/1999 | Wasserman |
| 5,867,604 A | 2/1999 | Ben-Levy et al. |
| 5,877,721 A * | 3/1999 | Tsang ...................... G01S 7/292 342/36 |
| 5,878,152 A | 3/1999 | Sussman |
| 5,912,984 A | 6/1999 | Michael et al. |
| 5,953,448 A | 9/1999 | Liang |
| 5,969,819 A | 10/1999 | Wang |
| 5,982,927 A | 11/1999 | Koljonen |
| 5,991,461 A | 11/1999 | Schmucker et al. |
| 5,995,232 A | 11/1999 | Van Der Ven |
| 5,999,266 A | 12/1999 | Takahashi et al. |
| 6,028,673 A | 2/2000 | Nagasaki et al. |
| 6,061,476 A | 5/2000 | Michani |
| 6,081,613 A | 6/2000 | Ikurumi et al. |
| 6,084,712 A | 7/2000 | Harding |
| 6,180,935 B1 | 1/2001 | Hoagland |
| 6,185,273 B1 | 2/2001 | Sperschneider |
| 6,201,892 B1 | 3/2001 | Ludlow et al. |
| 6,232,724 B1 | 5/2001 | Onimoto et al. |
| 6,268,923 B1 | 7/2001 | Michniewicz et al. |
| 6,269,197 B1 | 7/2001 | Wallack |
| 6,303,916 B1 | 10/2001 | Gladnick |
| 6,307,210 B1 | 10/2001 | Suzuki et al. |
| 6,445,813 B1 | 9/2002 | Ikurumi et al. |
| 6,496,254 B2 | 12/2002 | Bostrom et al. |
| 6,522,777 B1 * | 2/2003 | Paulsen ............... G01B 11/2513 356/237.2 |
| 6,549,647 B1 | 4/2003 | Skunes et al. |
| 6,577,405 B2 | 6/2003 | Kranz et al. |
| 6,750,899 B1 | 6/2004 | Fishbaine et al. |
| 7,239,399 B2 | 7/2007 | Duquette et al. |
| 8,064,068 B2 | 11/2011 | Fisher et al. |
| 2001/0025924 A1 * | 10/2001 | Uto ....................... G01N 21/956 250/307 |
| 2001/0033386 A1 | 10/2001 | Kranz et al. |
| 2002/0018219 A1 * | 2/2002 | Hallerman ............. G01N 21/88 356/604 |
| 2002/0154303 A1 * | 10/2002 | Maeda ............... G01N 21/8806 356/394 |
| 2003/0110610 A1 * | 6/2003 | Duquette ........... H04N 13/0207 29/407.09 |
| 2005/0122308 A1 | 6/2005 | Bell et al. |
| 2006/0033922 A1 | 2/2006 | Sperling et al. |
| 2006/0203096 A1 | 9/2006 | LaSalle et al. |
| 2007/0070336 A1 * | 3/2007 | Maeda ............... G01N 21/8806 356/237.2 |
| 2007/0120977 A1 | 5/2007 | Duquette et al. |
| 2008/0100843 A1 * | 5/2008 | Kono ................. G01N 21/8806 356/369 |
| 2009/0190139 A1 | 7/2009 | Fisher et al. |
| 2010/0007896 A1 * | 1/2010 | Fishbaine .......... G01N 21/8806 356/603 |
| 2010/0195114 A1 | 8/2010 | Mitsumoto et al. |
| 2010/0268069 A1 * | 10/2010 | Liang .................... G06T 7/521 600/425 |
| 2011/0316978 A1 | 12/2011 | Dillon et al. |
| 2013/0016154 A1 | 1/2013 | Imamura et al. |
| 2014/0002828 A1 * | 1/2014 | Laffargue ............. G01F 17/00 356/627 |
| 2014/0132953 A1 | 5/2014 | Jeong |
| 2014/0198185 A1 | 7/2014 | Haugen et al. |

FOREIGN PATENT DOCUMENTS

| | | | | |
|---|---|---|---|---|
| DE | 195 11 160 | | 10/1996 | |
| EP | 0453977 A2 | | 10/1991 | |
| EP | 0660078 A1 | | 6/1995 | |
| KR | 1020050044446 | | 5/2005 | |
| KR | 1020070119603 | | 12/2007 | |
| WO | 98/59490 | | 12/1998 | |
| WO | WO9912001 | | 3/1999 | |
| WO | WO9924786 | | 5/1999 | |
| WO | WO 0038494 | * | 6/2000 | ............. H05K 13/08 |
| WO | WO0038494 | | 6/2000 | |
| WO | WO 0038494 A2 | * | 6/2000 | ......... H04N 13/0239 |
| WO | 01/06210 | | 1/2001 | |
| WO | 01/54058 | | 7/2001 | |
| WO | WO0154068 A2 | | 7/2001 | |
| WO | WO201209 A1 | | 1/2002 | |
| WO | WO0201210 A1 | | 1/2002 | |
| WO | WO 03043400 A1 | | 5/2003 | |
| WO | WO2009094489 | | 7/2009 | |
| WO | WO2011037905 | | 3/2011 | |

OTHER PUBLICATIONS

Office Action for Korean Patent Application No. 10-2015-7021891 dated Sep. 12, 2016, 6 pages. No English Translation Available.
Office Action for U.S. Appl. No. 14/514,838 dated Sep. 30, 2016, 28 pages.
First Office Action for Chinese Patent Appiication No. 201480005092.0 dated Dec. 5, 2016, 19 pages with English Translation.

* cited by examiner

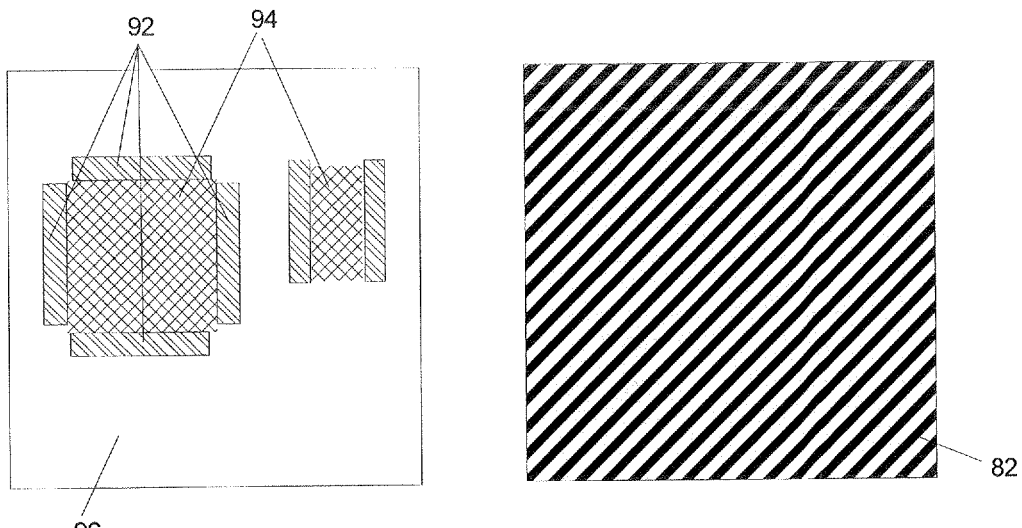
Fig 8a
Fig 8b
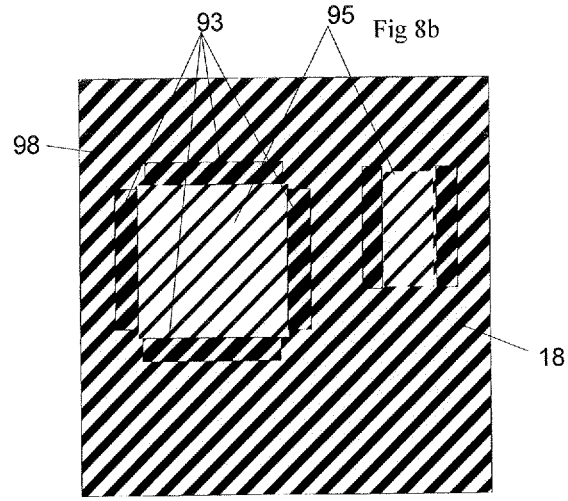
Fig 8c

ENHANCED ILLUMINATION CONTROL FOR THREE-DIMENSIONAL IMAGING

CROSS-REFERENCE TO RELATED APPLICATION

The present application is based on and claims the priority of provisional application Ser. No. 61/816,990, filed Apr. 29, 2013, the contents of which is hereby incorporated by reference in its entirety.

COPYRIGHT RESERVATION

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND

Circuit boards that carry electronic integrated circuits and discrete electronic components are well known. A circuit board substrate is prepared with predetermined conductor paths and pads for receiving the leads of electronic components such as integrated circuit chips, resistors or capacitors. During the circuit board assembly process, solder paste deposits are placed onto the board substrate at appropriate positions. The solder paste deposits are usually applied by placing a stencil screen onto the substrate, applying solder paste through the stencil openings and removing the stencil from the substrate. The circuit board electronic components are then positioned onto the substrate, preferably with a pick and place machine, with leads of the electronic components placed on the respective solder paste deposits. The circuit board is passed through an oven after all of the components are positioned on the substrate to melt the solder paste deposits thus creating an electrical as well as mechanical connection between the components and the substrate.

The size of the solder paste deposits and electronic components and the accuracy with which they must be placed on the substrate has become increasingly smaller and tighter with the increased emphasis on miniaturization in the electronics industry. Solder paste deposit heights can be as small as 50 microns and the height of the solder paste brick must often be measured to within 1 percent of the designed height and size. The center-to-center spacing between solder bricks is sometimes as little as 200 microns. Too little solder paste can result in no electrical connection between the lead of an electronic component and the pad of the circuit board substrate. Too much paste can result in bridging and short-circuiting between the leads of a component. Discrete electronic components such as resistors and capacitors can be as small as 200×400 microns and leads on micro ball grid array components can have a center-to-center spacing less than 300 microns.

A single circuit board can cost thousands and even tens of thousands of dollars to manufacture. Testing of a circuit board after the fabrication process is complete can detect errors in solder paste placement and component placement and lead connection, but often the only remedy for a faulty board is rejection of the entire board. In addition, with the miniaturization of components, visual inspection of the circuit board, even with optical magnification, is unreliable. It is accordingly imperative that a circuit board be inspected during the fabrication process so that improper solder paste placement can be detected prior to the placement of the electronic components onto the substrate. Such in-process solder inspection reduces the cost of failure since expensive components have not yet been placed onto the circuit board.

After placement, it is also important to inspect the components to ensure proper placement of the components. Improperly placed components, missing components or poor solder joints are typical defects introduced during the placement of the components and reflow of the solder paste. After reflow, proper placement of the components and the quality of the reflowed solder junctions can be inspected using an automated optical inspection system to ensure that all components are properly soldered and connected to the circuit board. Current optical inspection systems use 2D video images of the circuit board to detect defects. However, optical inspection systems that detect 3D height images of the circuit board make possible or otherwise improve the detection of placement defects such as lifted leads, package coplanarity, and component tombstones and billboards.

The use of white light phased profilometry is a well-known technique for optically acquiring topological surface height images of circuit boards. However, current circuit board inspection sensors that employ phased profilometry have some limitations. Typical phase profilometers used to acquire topological surface height image of circuit boards generally use triangulation principles combined with structured light to determine the height of the surface at every pixel defined by the sensor's camera. One limitation of using triangulation sensing to produce a height image of a circuit board is that the incident angle of the pattern projection optical axis and image sensing optic axis are different. If the circuit board has height features that have an edge slope large enough that they occlude either the pattern projection optical axis or image sensing optical axis relative to some area on the surface, the sensor will not be able to measure those areas of the circuit board.

One approach, to mitigate the triangulation shadow effect is to use multiple pattern projection sources with a normally incident camera. Each of the sources projects a structured pattern onto the circuit board from different incident angles. If one pattern projection source is occluded, or otherwise blocked, from an area of the test surface, there is a high probability that one of the other pattern projection source will be able to illuminate that area. To acquire a non-occluded height image, the camera acquires images from each of the pattern projection sources serially and then combines the results of the multiple height images to ensure ail areas of the linage contain valid height data. One disadvantage to this approach is that multiple image acquisition cycles are required to generate a single height image which slows down the overall acquisition process when compared to a sensor that uses a single source. Implementation of multiple, source white light phase triangulation sensors requires the pattern projection sources to be turned on separately so that the image from one source, followed by acquisition of an image from another source, can be acquired in sequence by the camera. This operation will typically require two or more image acquisition cycles of the sensor in order to acquire height image field of view (FOV).

In prior art phase profilometers, the structured light is characteristically generated by imaging a reticle consisting of a fixed chrome-on-glass pattern onto the circuit board. To acquire a height image, a sequence of patterned images are required, each of the images being a shifted version of the previous image. Typically, the structured pattern is a sinusoidal intensity pattern and the sequence of images are the same sinusoidal pattern; each image of the sequence shifted relative to the other images of the sequence some known fraction of the sinusoidal period. Usually, the phase shift in the sequence of images is created by physically moving the reticle within the sensor. One disadvantage to utilizing a chrome-on-glass reticle is that changing the frequency or orientation of the structured light requires replacing the reticle, changing the magnification of the pattern projection optics or both. Additionally, physically moving a glass reticle within the sensor requires expensive mechanical motion components. Also, the intensity or modulation depth of the sinusoidal pattern is fixed and cannot be changed.

Generating height images of circuit boards with a white light structured light sensor using a chrome-on-glass reticle restricts the usefulness of the resulting height images. Circuit boards, especially with mounted components, require a large height measurement range to accommodate tall components. Also, the surface of circuit boards is fabricated with many different materials, each with different optical characteristics and reflectivities. In some cases, the wide range of reflectivities on the surface of a circuit board is larger than can be detected by typical cameras. Reflowed solder, silk screen printing and metal traces are examples of bright objects on a circuit board. Dark solder mask material and component bodies are examples of very dark areas. Using a fixed chrome-on-glass reticle to illuminate the circuit board does not provide any flexibility in changing the measurement range or the amount of light projected on the circuit board.

Providing a multiple viewpoint triangulation sensor for generating height images of a circuit board using phased structured light that does not have the associated cost or speed penalty that is present in the current state of the art for multiple source phase height image sensors would represent a useful advance to high-speed three-dimensional inspection of circuit boards.

Coupled with the multiple viewpoint triangulation sensor, providing a means to change the frequency, orientation and type of the structured light pattern in real time without physically moving the reticle would allow the sensor to change characteristics without modifying the sensor hardware and increase the reliability of the sensor. In addition to changing the frequency and orientation of the structured light pattern, providing a means to modify the intensity of the structured light pattern in select areas of the sensor's field of view would enhance the dynamic range of the sensor. Also, providing a means to prevent light from illuminating selected areas in the field of view would reduce the effects of multiple path reflections which cause errors in height images of circuit boards.

SUMMARY

A system for sensing a three-dimensional topology of a circuit board is provided. An illumination source projects an illumination pattern from a first angle of incidence. A first camera acquires an image of the structured light pattern on the circuit board from a second angle of incidence. A second camera simultaneously acquires an image of the structured light pattern on the circuit board from a third angle of incidence, the third angle of incidence differing from the second angle of incidence. A controller is coupled to the illumination source and to the at least two camera devices. The controller generates a height topology of the circuit board based on images acquired from the at least two camera devices of the structure light illuminator.

The use of multiple cameras can be extended to more than two cameras. Three or four cameras can be configured to image the same area of the circuit board with each having a different angle of incidence. Combining the height images from the at least two cameras improves the performance of the height image sensor by reducing noise generated from a single imaging device and removing erroneous and missing height data caused by shadows and glints that are possible with a single image device based triangulation sensor.

In each embodiment of the present invention, the performance of the height image sensor is enhanced by using a digital structured light projector to enhance the dynamic range of the sensor to accommodate the wide range of reflectivities found on circuit boards. For one embodiment of the present invention the intensity of the structured light is varied as a function of the reflectivities found in the field of view of the sensor. By varying the intensity of the structured light, in a single exposure, dark areas of a circuit board can be illuminated with more light and bright areas of the circuit board can be illuminated with less light. Therefore, in a single exposure, an image can be captured by the sensor's cameras that match the camera's dynamic range.

In another embodiment of the present invention, the performance of the height image sensor is further enhanced by using a digital structured light projector to mask light from illuminating areas of a circuit board that cause multipath reflections. By blocking light to the areas of the circuit board that cause multipath reflections, height image errors caused by multipath reflections are eliminated.

In each embodiment, a controller is coupled to the illumination source and to the cameras. The controller generates a height topology of the circuit board based on images of the structured light acquired from the cameras. The controller is configured to program the structured light source to project a light pattern onto a target including programming the intensity of the projected structured light pattern, acquire images of the projected light pattern from the each of the cameras, generate a height image and a video image from images acquired from each of the cameras, and combine separated height and video images into composite height and video images.

BRIEF DESCRIPTION OF THE DRAWINGS

FIGS. 8*a*-8*c* demonstrate the process of modifying the structured light to match the structured, light intensity to the circuit board's reflectivity.

DETAILED DESCRIPTION

Figure 1:
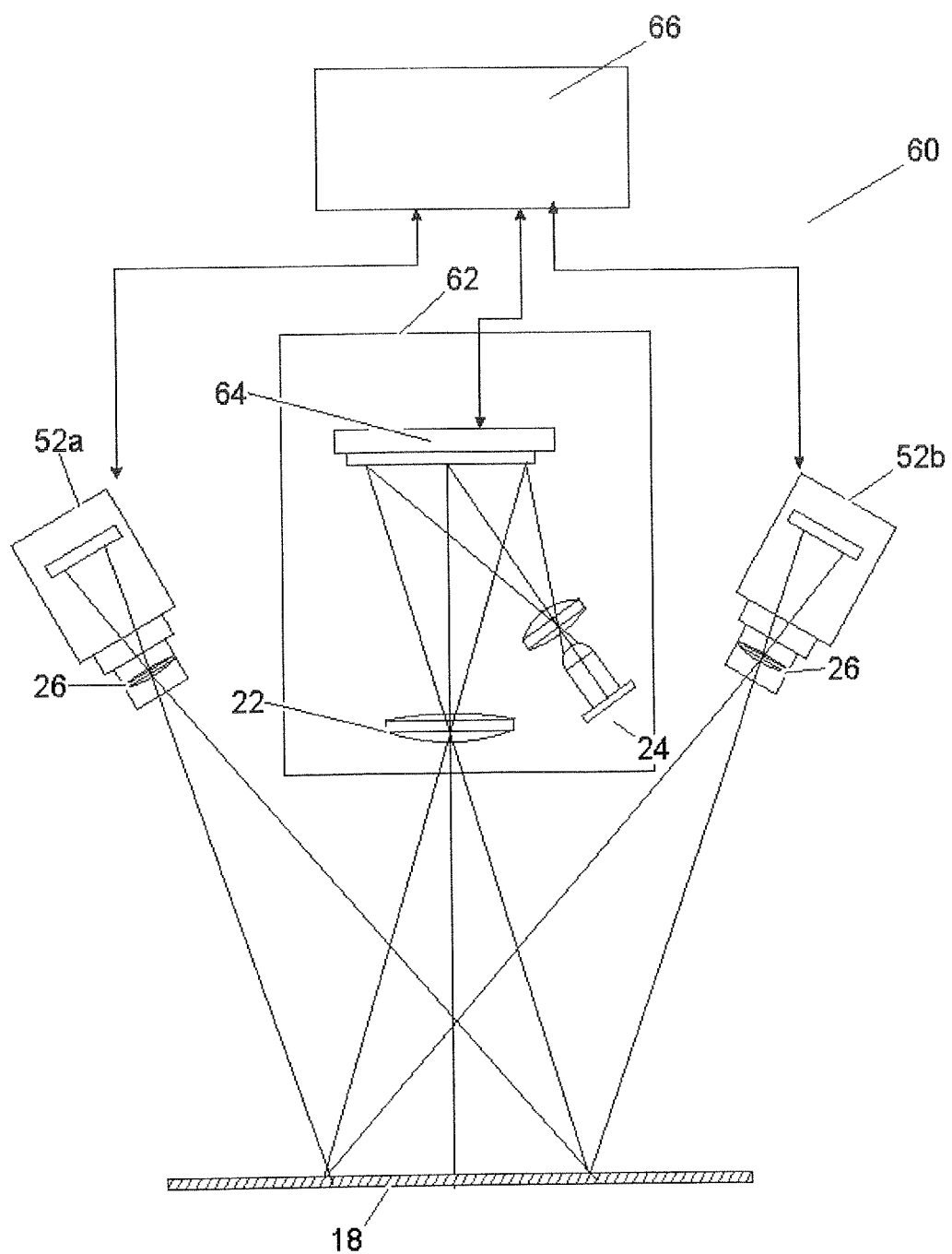
FIG. 1 is a diagrammatic view of multi-camera sensing system for three-dimensional imaging using phase structured light generated by a spatial light modulator in accordance with an embodiment of the present invention

FIG. 1 is a diagrammatic view of a multiple imaging device height image sensor 60 for three-dimensional imaging of circuit board 18 using phased structured light in accordance with an embodiment of the present invention. A pattern projection source 62 is coupled to controller 66 and projects structured light pattern 30 (shown in FIG. 2) onto circuit board 18 by imaging a spatial light modulator (SLM) 64 with imaging lens 22. In a preferred embodiment of the present invention, SLM 64 is a device available from Texas Instruments (e.g. TI part number DLP5500). This device incorporates an array of digital micro mirrors (DMDs) which are individually addressable to form an arbitrary image on the surface. In operation, the required structured light pattern 30 is programmed on the DMD array by controller 66. The programmed image causes each of the micro mirrors to tilt to one of two positions which correspond to the pixel intensity value of the image at the individual mirror's location. For pixels that are high brightness, the tilted DMD reflects the light from light source 24, through imaging lens 22 to circuit board 18 producing a bright pixel. For pixels that correspond to low brightness in the structured light pattern 30, the tilt of the DMD mirror reflects light from light source 24 away from the imaging lens 22 producing a dark pixel in structured light pattern 30. By changing the programmed image sent to the DMD, the required sequence of structured light images can be generated. SLM 64 is illuminated using bright light source 24 such as a white light LED. Two cameras 52*a*, 52*b* are coupled to controller 66 and are configured to simultaneously acquire an image of the circuit board 18 illuminated with structured light pattern 30. Cameras 52*a*, 52*b* can be any one of several image sensing technologies used in machine vision such as CCD or CMOS detectors coupled with imaging lens 26 that images the circuit board unto the detector. The difference between the optical axis incidence angles of pattern projection source 62 and the cameras 52*a*, 52*b* represent the triangulation angle of the height sensor.

In operation, light source 24 illuminates SLM 64 and pixels that are programmed with high brightness values reflect light through imaging lens 22. Imaging lens 22 projects the light from SLM 64 onto the circuit board 18. Typically, the sequence of structured light patterns used to acquire a single height image is a series of sinusoidal intensity patterns with each pattern of the series differing only in the phase or position of the sinusoidal pattern. Other suitable structured light patterns can also be used such as binary gray code patterns and pseudo random patterns. Simultaneous to projecting the first structured light pattern, both cameras 52*a*, 52*b* acquire a first image of the circuit board 18. The projection pattern programmed into SLM 64 is then changed to a second sinusoidal pattern with a relative phase shift of an equivalent distance of a fractional phase distance of the first sinusoidal pattern and cameras 52*a*, 52*b* acquire a second image. Finally, the projection pattern programmed into SLM 64 is then changed to a third sinusoidal pattern with a relative phase shift of an equivalent distance of a fractional phase distance of the first and second sinusoidal patterns and cameras 52*a*,52*b* acquire a third image.

The method of converting the intensity information from the multiple sinusoidal intensity pattern images to actual height images can be in accordance with any known techniques, such as those described in U.S. Pat. No. 6,750,899.

Using SLM 64 to generate a sequence of structured light images has advantages over using a mechanically shifted chrome-on-glass reticle typical of height sensors in prior art. With a chrome-on-glass reticle, structured light pattern 30 is fixed with the chrome-on-glass pattern and sequences of images with differing phases are generated by physically moving the reticle. Physically moving the reticle is costly and requires motion components that are prone to mechanical wear and ultimately failure. In addition, it is often required to change the sinusoidal pattern's period or orientation. By changing the sinusoidal pattern's period, the height range and height resolution of the height image sensor can be adjusted. Changing the height range of the sensor is particularly important when inspecting a circuit board after components have been placed since the height of the placed components can be higher than the height range of the sensor which is determined by the reticle pattern. Changing the chrome-on-glass reticle pattern requires physically replacing one reticle with another which typically cannot be accomplished during operation of the sensor.

With SLM 64, various patterns can be projected onto circuit board 18 by programming an array of numbers into the controller 66 representing the desired structured light pattern 30. Controller 66 directs SLM 64 to generate pattern 30. Projecting a sequence of structured light patterns with varying phases is simply accomplished by programming successive images by controller 66. By projecting successive images with SLM 64, a sequence of phase images is projected without physically moving the reticle. In addition, by changing the phase period of the pattern programmed by controller 66, the height resolution and height range of height imaging sensor 62 can be changed during the operation of the sensor.

Figure 2:
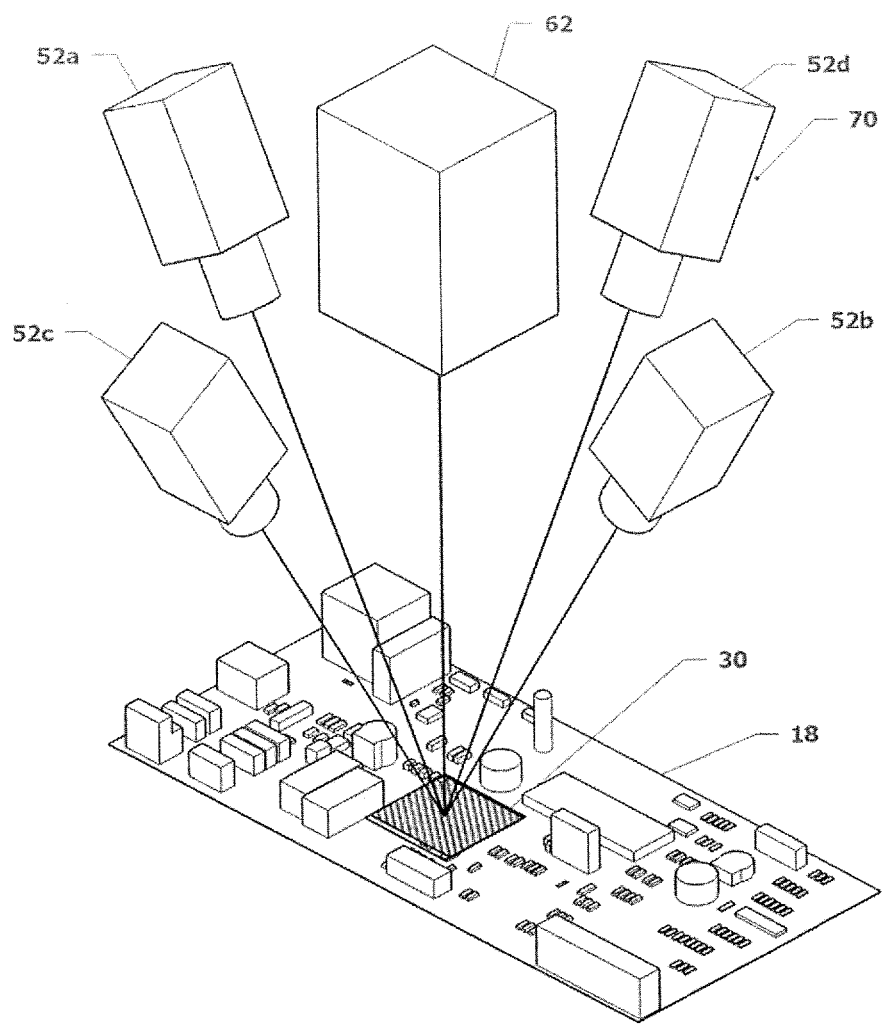
FIG. 2 is a diagrammatic view of a four-camera sensing system for height image sensor using phase structured light generated by a spatial light modulator in accordance with an embodiment of the present invention.

FIG. 2 is a diagrammatic view of a multiple imaging device height image sensor 70 for three-dimensional imaging of a circuit board using phased structured light in accordance with an embodiment of the present invention. In this embodiment, four cameras 52*a*, 52*b*, 52*c*, 52*d* are configured to simultaneously acquire images of sinusoidal structured light pattern 30 on circuit board 18 from Four distinct incident angles. Each of the four cameras' 52*a*, 52*b*, 52*c*, 52*d* incident angles form a triangulation angle relative to the projection incident angle of pattern projection source 62. Pattern projection source 62 projects sinusoidal structured light pattern 30 onto circuit board 18. Cameras 52*a*, 52*b*, 52*c*, 52*d* are preferably triggered simultaneously to acquire an image of the sinusoidal pattern 30. Patten projection source 62 projects a second sinusoidal pattern with a relative phase shift of an equivalent distance of a fractional phase distance of the first sinusoidal pattern and the four optical image sensors 52*a*, 52*b*, 52*c*, 52*d* are triggered simultaneously to acquire a second set of images. Finally, the projection pattern programmed into pattern projection source 62 is then changed to a third sinusoidal pattern with a relative phase shift of an equivalent distance of a fractional phase distance of the first and second sinusoidal patterns and cameras 52*a*, 52*b*, 52*c*, 52*d* each acquire a third image.

The images are sent to controller 66 which processes the images sets into a height image. Using four cameras improves the quality of the height map by decreasing imager noise effects and further eliminating the chance of an area of circuit board 18 to be in shadow or otherwise false height data. Since the images are acquired by cameras 52a, 52b, 52c, 52d simultaneously, there is no impact on multiple imaging device height image sensor's 70 acquisition speed.

Figure 3:
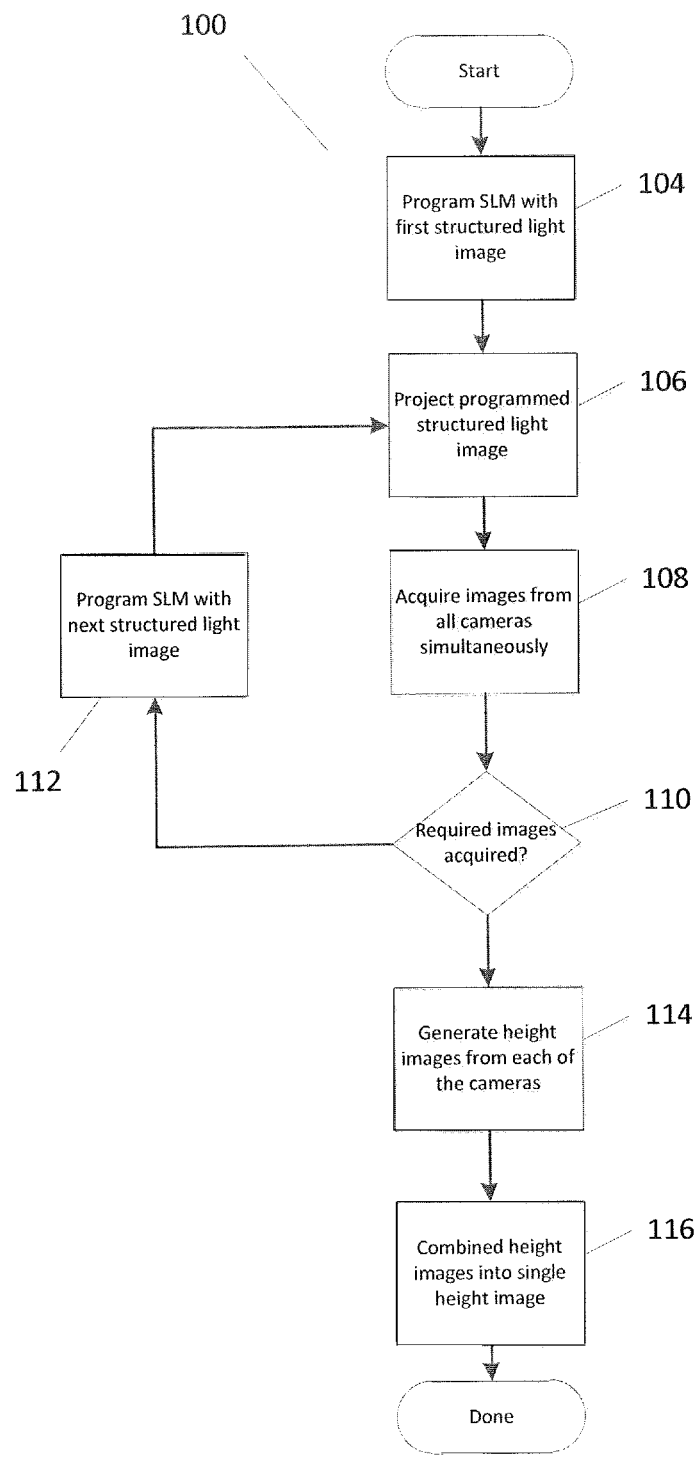
FIG. 3 is flow diagram that describes the process of acquiring images and generating height maps.

FIG. 3 shows a flow diagram that describes the process 100 used by controller 66 to acquire and process images from, cameras 52a, 52b, 52c, 52d to generate a combined height image. In step 104, SLM 64 is programmed to display the first structured light pattern. In step 106, an image of structured light pattern 30 as displayed by SLM 64 is projected onto the circuit board. The cameras are all triggered simultaneously in step 108 to acquire images of the structured light pattern from four different viewpoints. If more structured light patterns are required for the height reconstruction, SLM 64 is directed to display the next structured light pattern in step 112. Steps 106, 108 and 112 are repeated until the required number of patterns to generate a height image have been projected and acquired. In step 114, the controller generates a height image from the images acquired from each of the cameras. Each of the height images generated from images acquired from cameras 52a, 52b, 52c, 52d are combined into a single height image in step 116. Since the combined height image combines the height images from multiple camera viewpoints, the resulting height image has higher fidelity.

Figure 4:
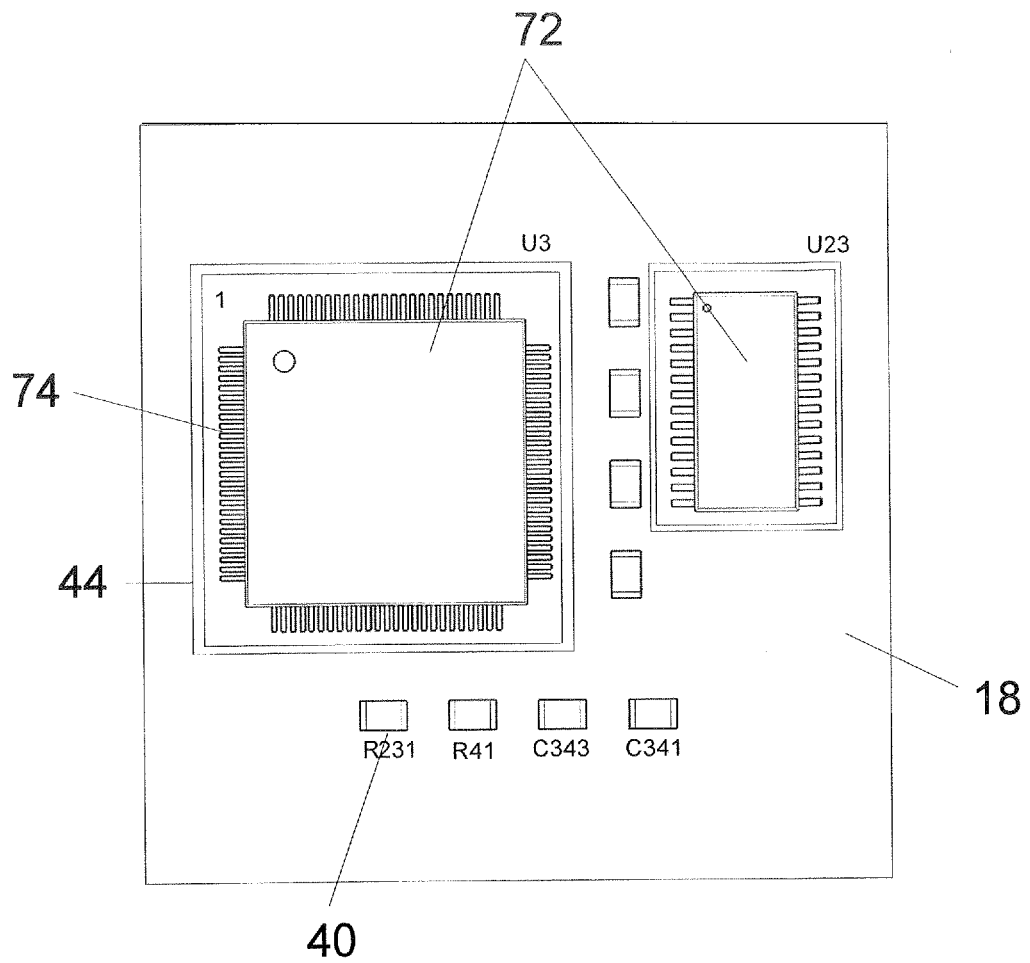
FIG. 4 is a diagrammatic view of a circuit board with placed components

FIG. 4 is a diagrammatic view of a circuit board 18 with placed components. Multi-pin packages 72 and discrete components 40 are typical of the components that are placed on circuit board 18. Other features including silk screen printing 44 are also located on circuit board 18.

Figure 5:
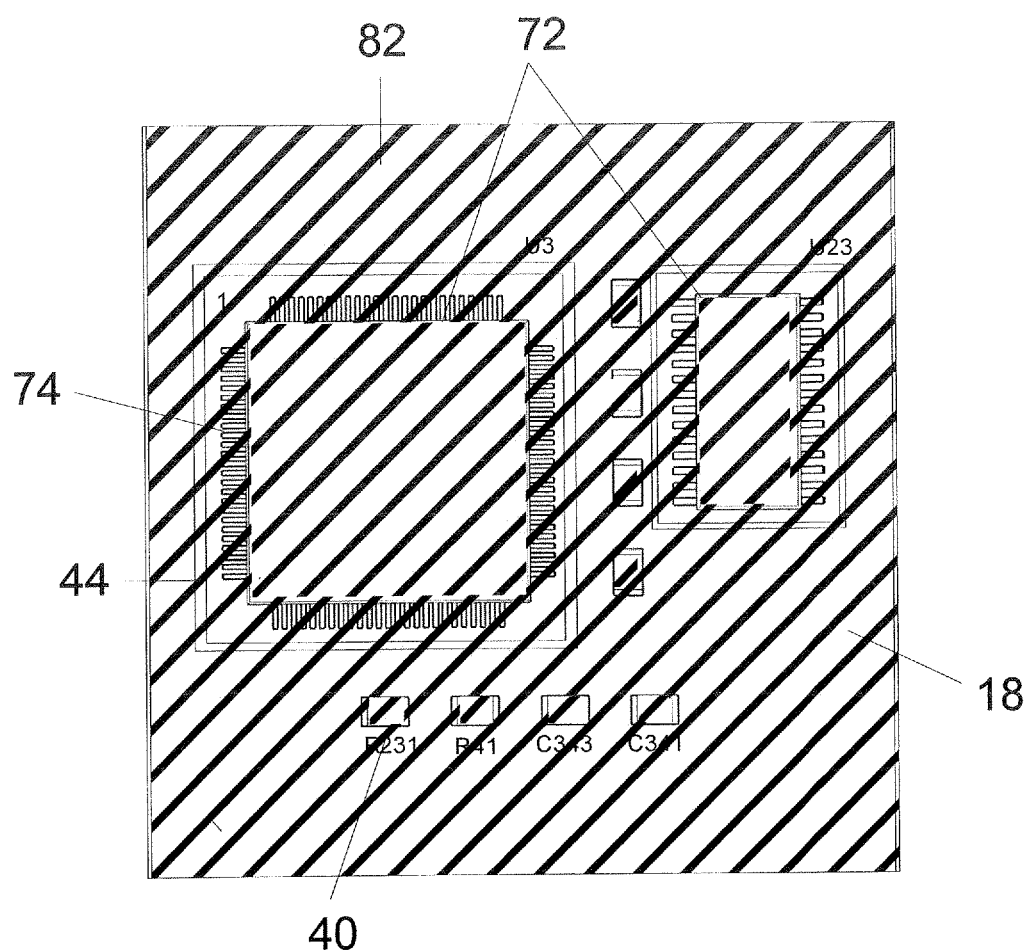
FIG. 5 is a diagrammatic view of a circuit board with placed components illuminated with a uniform intensity structure light pattern typical of structured light height image sensor systems

FIG. 5 is a view of circuit board 18 and mounted components 40, 72 illuminated with a uniform structured light pattern 82. Optically, the range of reflectivity that cameras 52 are required to image circuit board 18 is significant. Components 72, 40 are routinely formed with black resins and circuit board 18 can be coated with solder mask materials which reflect very little light back to cameras 52 while reflections from component leads 74 and silk screen 44 can be very bright, saturating cameras 52a. 52b, 52c, 52d. From the viewpoint of cameras 52a, 52b, 52c, 52d, the range of intensities required to acquire a high fidelity height image of circuit board 18 becomes larger than the dynamic range of the camera. This condition produces noisy height images where circuit board 18 is dark and erroneous height measurements where circuit board 18 is extremely bright. To accommodate dark areas or circuit board 18 and component bodies 72, the intensity of pattern projection source 62 should be increased. However, increasing the intensity of the projected light increases the probability of highly saturated image areas. Conversely, reducing the amount of light intensity to bright areas of circuit board 18 causes even greater image noise for these areas.

One technique used in prior art to increase the dynamic range of a height image sensor is to acquire several height images of the same field of view, each height image generated using a different overall light level and combining these height images into a final height image. One light level is configured to be bright which generates decent height images from the dark areas of circuit board 18 and components 72. A second light level is configured to be dimmer which allows the bright areas to be imaged without saturating cameras 52. However, this technique requires at least twice the number of images to be acquired per final height image which adversely affects the speed of the sensor.

Figure 6:
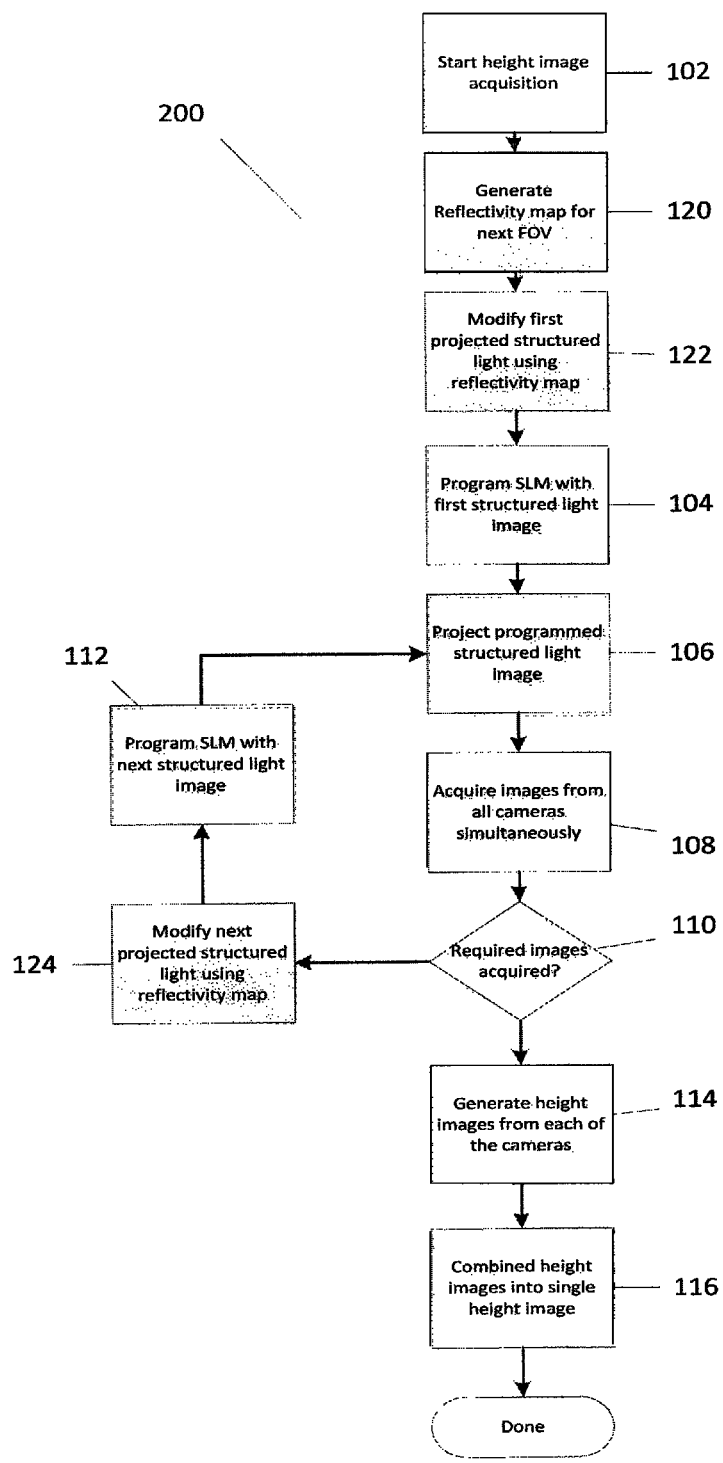
FIG. 6 is flow diagram that describes the process of acquiring images and generating height maps in accordance with the present invention.

Using the capabilities of SLM 64 as described in this embodiment of the present invention, the intensity of the uniform structured light pattern 82 can be modified spatially to increase the dynamic range of height range sensor 60. FIG. 6 is a flow diagram that describes the process 200 used by controller 66 for three-dimensional imaging of a circuit board using phased structured light in accordance with an embodiment of the present invention. Process 200 follows the same steps as process 100 shown in FIG. 3 except for the steps of modifying the projected structured light to increase the dynamic range of the sensor. First, in step 120, the reflectively of circuit board 18 is determined. The method of how the reflectively is determined is described below. In step 122, the intensity of the projected structured light pattern 82 is spatially modified. In dark areas of the image, the intensity of uniform structured light pattern 82 is increased. In bright areas of the image, the intensity of uniform Structured light pattern 82 is decreased. For multiple pattern projection images, the subsequent pattern images are modified using the same modifications as shown in step 124.

Figure 7:
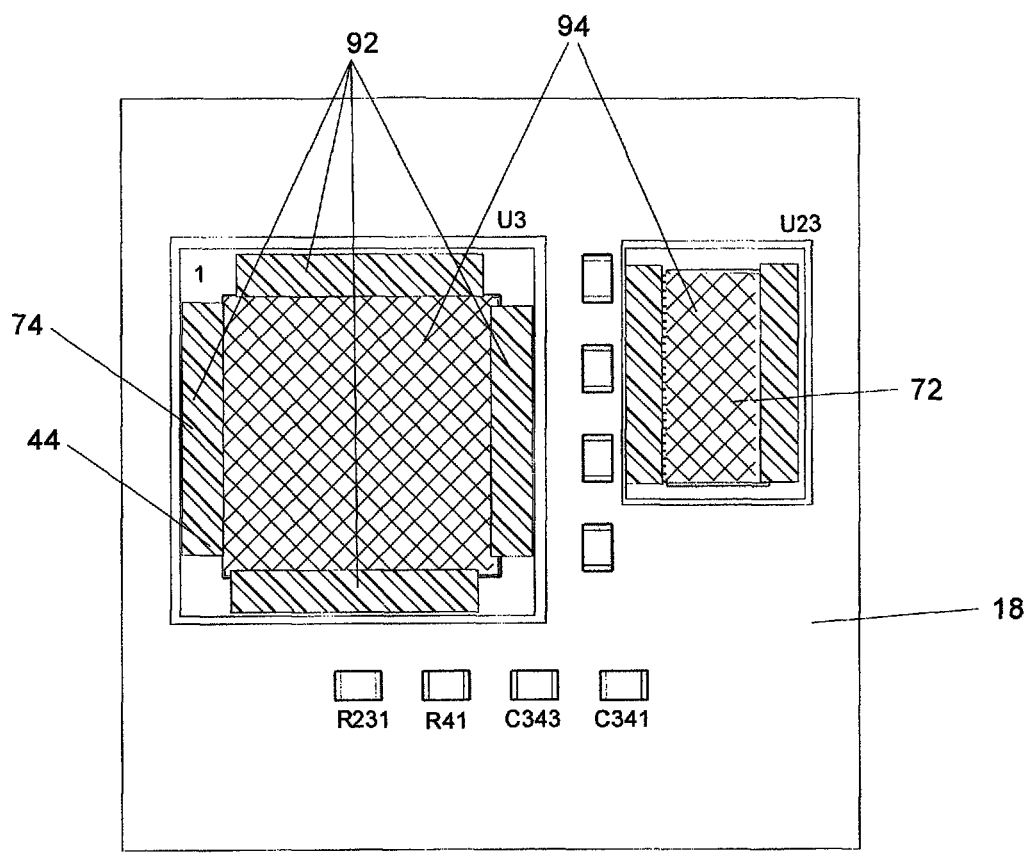
FIG. 7 is a diagrammatic view of a circuit board with areas of low reflectivity and high reflectivity highlighted.

In step 120, the reflectively of circuit board 18 is determined. FIG. 7 shows an example of a reflectively map of circuit board 18. Typical of circuit boards with mounted electronic components, bright reflectivity areas 92 can be identified in the areas component leads 74. Dark areas in the images can also be identified on the component bodies 94. Using these predetermined areas 92, 94, the projected image is be modified to match the reflectivities of these areas. Areas of bright and dark reflectivities can be determined from the design layout of the board. Design layout is typically derived from computer aided design (CAD) files used in the assembly of circuit board 18. Alternatively, prior images of circuit board 18 can be acquired and bright and dark areas of circuit board 18 can be determined using image analysis techniques.

FIGS. 8a-8c are diagrammatic views of the process of combining the reflectivity map 96 with the uniform illumination pattern 82 to generate a modified illumination pattern 98. FIG. 8a shows the reflectivity map 96 generated from information of the circuit board 18. Bright areas 92 and dark areas 94 are identified in the map. Modified pattern 98 is generated by increasing intensity of the uniform pattern 82 in dark areas 94 and decreasing intensity of uniform pattern 82. The resulting structured light pattern 98 is shown in FIG. 8c. Areas 93 are shown in FIG. 8c with reduced intensity and areas 95 are shown with increased intensity. Using modified pattern 98, the resulting images acquired by cameras 52 will be uniformly exposed across fee image which results in higher quality height images. Using this technique, the number of pattern images required to acquire height maps does not increase to accommodate large reflectivity changes found on circuit boards.

Figure 9:
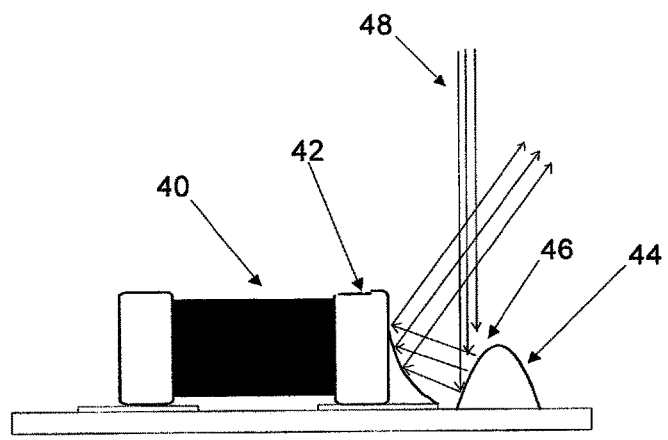
FIG. 9 is a diagrammatic view of a typical multipath reflection found on a circuit board.

In the second embodiment of the present invention, pattern projection source 62 generates a spatially modulated structured light pattern that eliminates the effects of multipath reflections. Multipath reflection is shown diagrammatically in FIG. 9. Light incident 48 on a circuit board from pattern projection source 62 is reflected off of printed silk screen 44. Silk screen printing on circuit boards is typically bright white and will reflect light efficiently. The light reflected 46 from silk screen 44 is further reflected off of a component lead 42 which is typically coated with shiny reflowed solder. If the alignment of silk screen 44 and component lead 42 is in the triangulation plane of cameras 52, the reflected light off of end cap 42 is imaged back to the camera 52. The light from multipath reflections does not follow the same path as light that undergoes a single reflection which causes errors in the height image.

Figure 10:
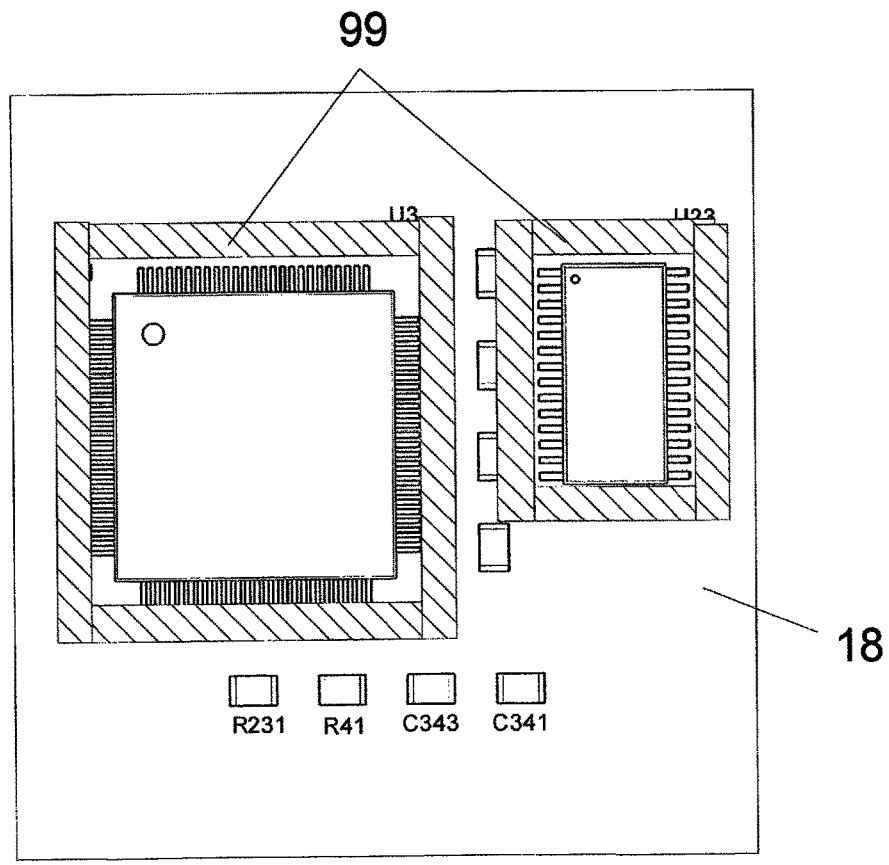
FIG. 10 is a diagrammatic view of a circuit board with areas of the circuit board that cause multipath reflections highlighted.
Figure 11A:
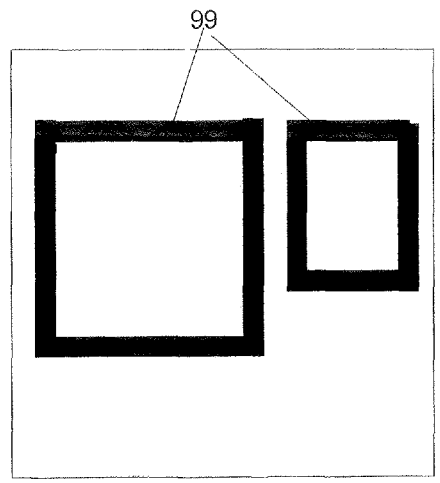
FIGS. 11*a*-11*d* demonstrate the process of modifying the structured light to mask areas where multipath reflections occur.
Figure 11B:
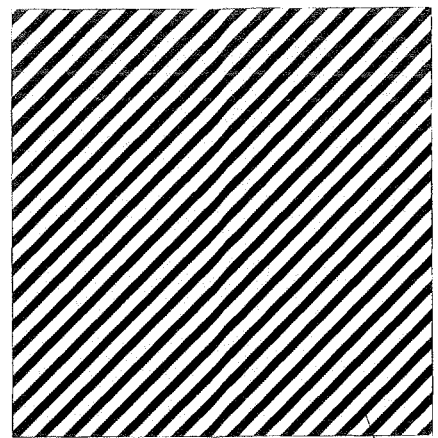
Figure 11C:
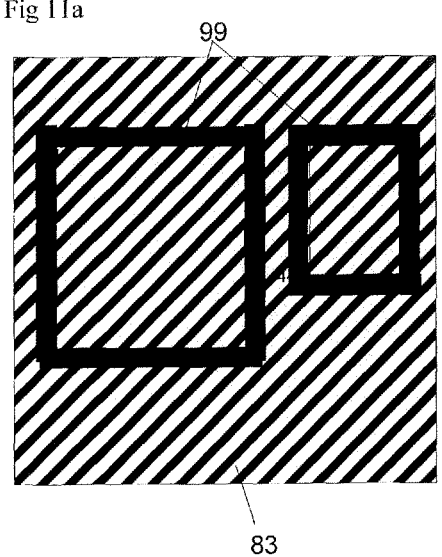
Figure 11D:
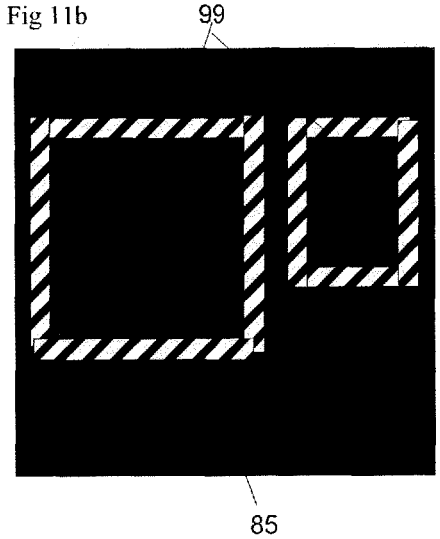

To eliminate the cause of multipath reflections, areas of the uniform structured light pattern 82 can be masked so that no light will illuminate the circuit board in these areas. Shown in FIG. 10, areas 99 can be identified that cause multipath reflections. In FIG. 10, this area is the silk screen 44 near component leads 74. The position of the silk screen or other potential areas of multipath reflections can be determined using previous captured images of circuit board 18 or CAD design data. Additionally, areas of multipath reflections can be deduced by comparing height and intensity images from the multiple cameras 52. Multipath reflections typically will only affect one camera so by comparing images from multiple cameras, areas of multipath reflections can be found by determining locations where one camera's height image differs from another camera's height image In FIG. 11, the process of combining areas 99 where multipath reflections are possible with pattern 82 to eliminate height image errors is shown. FIG. 11*a* shows the mask that identifies areas 99 of possible multipath reflections. FIG. 11*b* shows uniform structure light pattern 82. To eliminate multipath reflections, a structured light pattern 83 is generated in which the areas 99 are programmed such that no light will be projected (FIG. 11*c*). Generating a height map with structured light pattern 83 will block light from illuminating the silk screen which will eliminate multipath reflections. However, areas of the circuit board within the masked areas 99 will not be represented in the resulting height image. To generate a height image of areas 99, a second set of illumination patterns 85 can be generated that only illuminate areas 99. By combining the height images generated using the modified illumination pattern 99 shown in FIG. 11*c* and the second modified illumination pattern 85 shown in FIG. 11*d*, a full height image of circuit board 18 will be generated without errors caused by multipath reflections.

Although the present invention has been described with reference to preferred embodiments, workers skilled in the art will recognize that changes may be made in form and detail without departing from the spirit and scope of the invention. For example, while embodiments of the present invention generally describe the utilization of a CMOS detector, any suitable image acquisition device including a CCD array can be used. Also, while embodiments of the present invention generally describe the utilization of DMD device, other SLM technologies, such as Liquid Crystal Display Devices (LCD) and Liquid Crystal on Silicon (LCOS) SLM can also be used to produce programmable structured light patterns. In the present invention, these programmable structured light patterns were described as sinusoidal intensity patterns. However, there are several other suitable patterns such as binary gray code patterns and pseudo random structured patterns.

What is claimed is:

1. A system for generating a three-dimensional height image of a circuit board, the system comprising:
    an illumination source configured to generate a series of patterned illuminations on the circuit board;
    at least one camera configured to acquire images of the series of patterned illuminations from a camera point of view;
    a controller configured to process design layout information relative to the circuit board to identify an area of the circuit board having multipath reflections and, in response to the identified area having multipath reflections, generate an altered illumination pattern, wherein the altered illumination pattern blocks light from the area; and
    wherein the controller is coupled to the illumination source and the at least one camera, the controller being configured to generate a height image of the circuit board by acquiring a sequence of images with the at least one camera using the altered illumination pattern.

2. The system of claim 1, wherein the circuit board contains solder paste deposits prior to component placement.

3. The system of claim 1, wherein the circuit board is populated with electrical components.

4. The system of claim 1, wherein the design layout information is provided by at least one CAD file of the circuit board.

5. A method of three-dimensionally mapping an image of a circuit board surface, the method comprising:
    projecting at least one illumination pattern onto the circuit board surface from a first point of view;
    capturing a first image of the circuit board surface from a second point of view with a first camera while the at least one illumination pattern is disposed upon the circuit board surface;
    capturing a second image of the circuit board surface from a third point of view with a second camera while the at least one illumination pattern is disposed upon the circuit board surface;
    comparing the first and second images to identify an area of the circuit board having multipath reflections;
    generating a modified illumination pattern, at least in part, by modifying an intensity of the at least one illumination pattern in response to the identification of the area of the circuit board having multipath reflections;
    capturing a third image while the modified illumination pattern is disposed upon the circuit board surface; and
    computing a height map of the circuit board surface based on the third image.

6. The system of claim 1 wherein the altered illumination pattern is generated at the illumination source.

\* \* \* \* \*